United States Patent
Hua et al.

(10) Patent No.: US 10,465,254 B2
(45) Date of Patent: Nov. 5, 2019

(54) METHOD FOR DETECTING AND TYPING HIGH-RISK HUMAN PAPILLOMAVIRUSES

(71) Applicant: Hangzhou DALTON BioSciences, Ltd., Zhejiang (CN)

(72) Inventors: Shaobing Hua, Zhejiang (CN); Jiefeng Hu, Zhejiang (CN); Xufeng Zhu, Zhejiang (CN); Yingjia Shou, Zhejiang (CN); Deqiang Li, Zhejiang (CN); Shuanlin Wei, Zhejiang (CN); Bin Han, Zhejiang (CN)

(73) Assignee: Hangzhou DALTON BioSciences, Ltd., Zhejiang (CN)

( * ) Notice: Subject to any disclaimer, the term of this patent is extended or adjusted under 35 U.S.C. 154(b) by 0 days.

(21) Appl. No.: 15/506,988

(22) PCT Filed: Aug. 28, 2015

(86) PCT No.: PCT/CN2015/088325
§ 371 (c)(1),
(2) Date: Feb. 27, 2017

(87) PCT Pub. No.: WO2016/029867
PCT Pub. Date: Mar. 3, 2016

(65) Prior Publication Data
US 2017/0253939 A1    Sep. 7, 2017

(30) Foreign Application Priority Data
Aug. 28, 2014    (CN) .......................... 2014 1 0431874

(51) Int. Cl.
*C12Q 1/6841* (2018.01)
*C12Q 1/6844* (2018.01)
*C12Q 1/6804* (2018.01)
*C12Q 1/70* (2006.01)
*C12Q 1/6816* (2018.01)

(52) U.S. Cl.
CPC ........... *C12Q 1/708* (2013.01); *C12Q 1/6804* (2013.01); *C12Q 1/6816* (2013.01); *C12Q 2600/156* (2013.01)

(58) Field of Classification Search
None
See application file for complete search history.

(56) References Cited

U.S. PATENT DOCUMENTS

2006/0051809 A1    3/2006    Nazarenko et al.
2012/0004128 A1    1/2012    Mallonee et al.

FOREIGN PATENT DOCUMENTS

| CN | 1814796 A | 8/2006 |
|---|---|---|
| CN | 101899497 A | 12/2010 |
| CN | 102367490 A | 3/2012 |
| CN | 102822353 A | 12/2012 |
| CN | 103694345 A | 4/2014 |
| WO | 2009129505 A2 | 10/2009 |

OTHER PUBLICATIONS

Arney et al. Molecular Diagnostics of Human Papillomavirus. Labmedicine, Sep. 2010, 41: 523-530.*
Lowe et al. HPV Genotype Detection Using Hybrid Capture Sample Preparation Combined with Whole Genome Amplification and Multiplex Detection with Lunninex XMAP. J Mol Diagn 2010, 12:847-853.*
Poljak et al. Commercially available assays for multiplex detection of alpha human papillomaviruses. Expert Rev. Anti Infect. Ther. 2010, 8(10), 1139-1162.*
"Digene HC2 High-Risk HPV DNA Test" (https://www.qiagen.com/us/shop//detection-solutions/hpv-testing/digene-hc2-high-risk-hpv-dna-test/#productdetails, obtained online Jun. 27, 2018).*
Sargent et al. Optimal Threshold for a Positive Hybrid Capture 2 Test for Detection of Human Papillomavirus: Data from the Artistic Trial. Journal of Clinical Microbiology, 2010, 48(2) : 554-558.*
GenBank: K02718.1. Human papillomavirus type 16 (HPV16), complete genome. Dated Mar. 18, 1994.*
GenBank: U31794.1. Human papillomavirus type 66, complete genome. Dated Oct. 18, 1995.*
Li, Jing et al. "Epidemiological Features of Human Papillomavirus (HPV) Infection among Women Living in Mainland China" Asian Pacific Journal of Cancer Prevention, vol. 14, 2013:4015-4023.
Remmink, Ans J. et al. "The Presence of Persistent High-Risk Hpv Genotypes in Dysplastic Cervical Lesions is Associated with Progressive Disease: Natural History up to 36 Months" Int. J. Cancer: 61,306-311 (1995): 306-311.
Bosch, F X, et al. "The Causal Relation between Human Papillomavirus and Cervical Cancer" J Clin Pathol 2002: 55: 244-265.

(Continued)

*Primary Examiner* — Nianxiang Zou
(74) *Attorney, Agent, or Firm* — Quarles & Brady LLP (57) ABSTRACT

The present invention relates to a method for detecting and typing high-risk human papillomavirus (HPV). A probe having a specific detection function for 14 types of high-risk HPV is disclosed, and a technology capable of detecting and typing high-risk HPV DNA is developed on the basis of a nucleic acid hybridization chemiluminescence immunoassay technology.

7 Claims, 1 Drawing Sheet
Specification includes a Sequence Listing.

(56) References Cited

OTHER PUBLICATIONS

Khan, Michelle J. et al. "The Elevated 10-Year Risk of Cervical Precancer and Cancer in Women With Human Papillomavirus (HPV) Type 16 or 18 and the Possible Utility of Type-Specific HPV Testing in Clinical Practice" Journal of the National Cancer Institute, vol. 97, No. 14, Jul. 20, 2005: 1072-1079.

Dillner, Joakim "The Serological Response to Papillomaviruses" Cancer Biology, vol. 9, 1999: pp. 423-430.

Frazer, Ian H. "Measuring Serum Antibody to Human Papillomavirus Following Infection or Vaccination" Gynecologic Oncology 118 (2010): 8-11.

Molijn, Anco et al. "Molecular Diagnosis of Human Papillomavirus (HPV) Infections" Journal of Clinical Virology 32S (2005): 43-51.

Walboomers, Jan M. M. et al. "Human Papillomavirus is a Necessary Cause of Invasive Cervical Cancer Worldwide" J. Pathol. 189 (1999): 12-19.

International Search Report issued in corresponding PCT Application No. PCT/CN2015/088325, dated Nov. 19, 2015, 4 pages.

Poljak, et al., Hybrid Capture II HPV Test Detects at Least 15 Human Papillomavirus Genotypes Not Included in Its Current High-Risk Probe Cocktail, Journal of Clinical Virology, 2002, 25:S89-S97.

Qiao, et al., A New HPV-DNA Test for Cervical-Cancer Screening in Developing Regions: A Cross-Sectional Study of Clinical Accuracy in Rural China, Lancet Oncology, 2008, 9:929-936.

European Patent Office, Extended European Search Report, Application No. 15836767.2, dated Mar. 1, 2018, 9 pages.

\* cited by examiner

METHOD FOR DETECTING AND TYPING HIGH-RISK HUMAN PAPILLOMAVIRUSES

CROSS-REFERENCE TO RELATED APPLICATIONS

This application represents the national stage entry of PCT International Application PCT/CN2015/088325 filed Aug. 28, 2015 and claims priority to Chinese Patent Application 201410431874.2 filed Aug. 28, 2014. The contents of this application are hereby incorporated by reference as if set forth in their entirety herein.

TECHNICAL FIELD

The invention relates to the field of biomedicine, particularly relates to a HPV DNA typing detection technology based on nucleic acid hybridization chemiluminescence immune technology and the application thereof.

BACKGROUND ART

Human papillomavirus (HPV) is an icosahedron DNA virus which belongs to papilloma genus A of Papillomaviridae family. The genome of the HPV is a double-stranded cyclic DNA with about 8000 base pairs, with all open reading frames (ORFs) encoded by one DNA strand. The HPV is divided into different types according to the less than 90% homology of the genomic nucleic acid sequence, the difference between the nucleic acid sequences of the virus genome in the same type at 2-10% is deemed as different subtypes, while in the same subtype, the viral genomic nucleic acid sequence difference less than 2%, is deemed as variant. Up to present, researchers have found nearly a hundred types of HPV. Different types cause different clinical manifestation and may be classified into different types according to the different tissue sites invaded: the skin-type and mucosal-type. The skin types include HPV1, 2, 3, 4, 7, 10, 12, 15 and the like, associated with common warts, flat warts, and plantar warts, etc., also include HPV 5, 8, 14, 17, 20, 36, 38, and the like associated with epidermodsplasia verruciformis. The mucosal type includes HPV6, 11, 13, 32, 34, 40, 42, 43, 44, 53, 54 and the like associate with infection in genitalia, anus, oropharynx, esophageal mucosa, and the like, and also includes HPV16, 18, 30, 31, 33, 35, 39 associated with cervical cancer, rectal cancer, oral cancer, tonsil carcinoma, etc., (Jenson A B et al. 1984, Human papillomavirus. In: Belshe R B, editor. Textbook of Human Virology. Littleton, M A: PSG-Wright; p 951-68). HPV can be classified into "high-risk" and "low-risk" types according to risk of human oncogenesis. Low-risk HPV, such as HPV 6, 11, 42, 53 and the like, are associated with infections at genital, anus, oropharynx, esophageal mucosa, and the like, and high-risk HPV is the main cause of cervical cancer and the like.

Famous German medical scientist, Harald zur Hausen, has found early in the 1970s that high-risk HPV infection is the cause of cervical cancer (zur Hausen H. 1977, Human papillomaviruses and their possible role in squamous cell carcinomas. Curr. Top. Microbiol. Immunol., 78: 1-30). His study confirms the direct correlation between the two, and thus got the Nobel prize in physiology or Medicine in 2008. Investigation on the tumor epidemiology in China by famous tumor epidemiology specialist Youlin Qiao and his team, Cancer Institute of Cancer Hospital, Chinese Academy of Medical Science discovered that the relevance between Chinese cervical disease (≥CIN2) and HPV infection can be up to 96-100% (Jing Li et al. 2013, Epidemiological Features of Human Papillomavirus (HPV) Infection among Women Living in Mainland China. Asian Pac J Cancer Prev, 14 (7): 4015-4023). Since the international workshop of the international agency for research on cancer (IARC) in 1995 HPV infection is considered the main cause of cervical cancer. The continuous infection of HPV has been considered an essential factor and main cause of cervical cancer pathogenesis. A lot of researches indicate that most cervical intraepithelial neoplasia (CIN) and almost all cervical cancer lesions have high-risk HPV infection (Remmink A J et al. 1995, The presence of persistent high-risk HPV genotypes in dysplastic cervical lesions is associated with progressive disease: natural history up to 36 months. Int J Cancer, 61(3): 306-11). It is noted that, the pathogenesis of cervical cancer generally needs to undergo continuous infection of HPV to different levels of CIN(CIN1-CIN3), and eventually develops into cervical cancer (Bosch F X et al. 2002, The causal relation between human papillomavirus and cervical cancer. J Clin Pathol, 55(4): 244-65). The process is generally relatively long and lasts for 10-15 years in average, which provides sufficient time for early discovery and blocking of cervical cancer and precancerous pathology thereof.

At present, world health organization (WHO) and international agency for research on cancer (IARC) classified 14 HPV subtypes (HPV16, 18, 31, 33, 35, 39, 45, 51, 52, 56, 58, 59, 66, and 68) as high-risk HPV types, and a large number of studies found that 70% of cervical cancer is caused by HPV16 and 18 (Khan M J et al. 2005, The elevated 10-year risk of cervical precancer and cancer in women with human papillomavirus (HPV) type 16 or 18 and the possible utility of type-specific HPV testing in clinical practice. J Natl Cancer Inst, 97(14): 1072-9). Therefore, the detection of high-risk HPV 16 and 18 infection has significantly important meaning in preventing cervical cancer.

So far, HPV cannot be cultured in vitro, and as the etiology relationship in cervical cancer and high-risk HPV getting more and more attention, high-risk HPV detection has been used to evaluate the risk of cervical cancer occurrence. In order to realize early diagnosis and timely treatment to prevent the occurrence of cervical diseases (including cervical cancer), research on HPV detection is necessary.

HPV antigen detection: after the human epidermis is infected by HPV, the capsid protein is synthesized by intracellular proliferation to become HPV antigen. The immune enzyme staining can be used for detecting HPV antigen protein L1 in infected tissue cells so as to know whether HPV infection exists or not. However, since the HPV antigen immunohistochemistry method can only identify the capsid protein of the cell nucleus, while such capsid protein appears only in one stage of HPV life cycle (in late-stage virions), the antigen expression quantity differs with the degree of pathological changes. Meanwhile, the method requires a large number of virions to generate a positive reaction. Therefore, the detection rate of this method is relatively low (Dillner J. 1999, The serological response to papillomaviruses. Semin Cancer Biol, 9: 423-30).

HPV antibody detection: after HPV infects human body, the human body induces an anti-HPV antibody, so that the anti-HPV antibody in serum can be detected. The detection of antibody is mainly used for detecting the HPV16E6 and E7 antibodies. Because the detection sensitivity is low and the antibody appears at the late stage of the disease, it is not suitable for early diagnosis of the disease. In addition, after human being is infected by HPV, the antibody produced by the body can be presented for a long time, the detection of HPV antibodies by serological method cannot determine whether the infection is recent or in the past. At the same time, because there are many types of HPV and the immunoreaction is not consistent, HPV antibody detection is rarely used. (Frazer I H. 2010, Measuring serum antibody to human papillomavirus following infection or vaccination. Gynecol Oncol, 118(1 Suppl): S8-11).

Traditional morphology methods and immunological methods cannot fully prove whether HPV infection exists or not, and the clinical sensitivity and the specificity are not desirable ideal, which will induce high false positive rate and false negative rate. The newly-developed detection methods detect HPV by using a molecular biological method, including method based on signal amplification and method based on template amplification. Methods based on template amplification are based on PCR, combined with different detection technologies, mainly comprise fluorescent PCR method, PCR combining membrane hybridization method, PCR combining reverse-point hybridization method, or PCR combining quantum dot technology (Anco Molijn et al. 2005, Molecular diagnosis of human papillomavirus (HPV) infections. J Clin Virol, 32 Suppl 1: S43-51).

The PCR-based method which is based on template amplification mainly has the following problems: (1) the PCR technology is a detection method by amplifying target DNA fragments, for which the laboratory environment and the relatively strict experimental operation level are relatively high; generally speaking, more than one virus besides HPV are tested in the PCR laboratory of a hospital, so that in the process of amplifying the target DNA, a large number of different types of viral DNA amplification fragments are easily generated, these fragments can react with each other due to mistakes and operation errors of laboratory environment, so that environmental pollution of the laboratory is caused, and false positive or false negative results will occur to cause misdiagnosis or missed diagnosis of the patient; (2) many products based on the PCR technology generally only detect the L1 region of the HPV genome, and research shows that In this way, 5-10% of cervical cancer will miss diagnosis, as a result false negative results will be generated (Walboomers et al 1999, Human papillomavirus is a necessary cause of invasive cervical cancer worldwide J Pathol, 189: 12-19); (3) There is competitive inhibition in PCR reactions. When a variety of subtype infection are presented in of a patient, only the subtype with relatively high proliferation amount can be amplified, and the subtype with less virus number can result in false negative results due to relatively low amplification; that is, if the number of the virus of high-risk subtypes infected by a patient is less than the number of the virus of low-risk subtype the result will be a negative result, so that misdiagnosis of the patient is caused; (4) The sensitivity and the specificity of the detection method of the PCR technology are mainly subjected to the influence of sample transportation and preservation conditions, variation of DNA sequence in same HPV subtype, loss of HPV DNA in extraction process, primer pair design, PCR product size, and PCR program design, among others.

In conclusion, the present field needs to further optimize the HPV detection method to develop a convenient and accurate product suitable for clinical application.

SUMMARY OF THE INVENTION

The invention aims to provide detection and typing method for high-risk human papillomavirus.

In a first aspect of the invention, a kit for high-risk HPV detection is provided, the kit comprises: virus-specific RNA probes targeted at HPV type 16, 18, 31, 33, 35, 39, 45, 51, 52, 56, 58, 59, 66 and 68.

In one preferred example, the virus-specific RNA probes targeted at HPV16 is a RNA sequence including the RNA sequence corresponding to the DNA sequences of 83-1558, 3193-4628, 5559-7154 of Genbank accession number k02718, or the RNA sequence complementary to such DNA sequence;

the virus-specific RNA probes targeted at HPV18 is a RNA sequence including the RNA sequence corresponding to the DNA sequences of 105-1593, 2376-3867, 5430-7136 of Genbank accession number X05015, or the RNA sequence complementary to such DNA sequence;

the virus-specific RNA probes targeted at HPV31 is a RNA sequence including the RNA sequence corresponding to the DNA sequences of 108-1463, 3564-4982, 5558-7072 of Genbank accession number HQ537666, or the RNA sequence complementary to such DNA sequence;

the virus-specific RNA probes targeted at HPV33 is a RNA sequence including the RNA sequence corresponding to the DNA sequences of 109-1654, 3789-5087, 5594-7093 of Genbank accession number M12732, or the RNA sequence complementary to such DNA sequence;

the virus-specific RNA probes targeted at HPV35 is a RNA sequence including the RNA sequence corresponding to the DNA sequences of 110-1476, 3452-4897, 5601-7109 of Genbank accession number X74477, or the RNA sequence complementary to such DNA sequence; and the virus-specific RNA probes targeted at HPV39 is a RNA sequence including the RNA sequence corresponding to the DNA sequences of 107-1608, 2654-4187, 5643-7160 of Genbank accession number M62849, or the RNA sequence complementary to such DNA sequence;

the virus-specific RNA probes targeted at HPV45 is a RNA sequence including the RNA sequence corresponding to the DNA sequences of 102-1543, 3421-4872, 5530-7149 of Genbank accession number X74479, or the RNA sequence complementary to such DNA sequence;

the virus-specific RNA probes targeted at HPV51 is a RNA sequence including the RNA sequence corresponding to the DNA sequences of 68-1476, 2875-4452, 5894-7431 of Genbank accession number M62877, or the RNA sequence complementary to such DNA sequence;

the virus-specific RNA probes targeted at HPV52 is a RNA sequence including the RNA sequence corresponding to the DNA sequences of 89-1565, 2459-4098, 5565-7154 of Genbank accession number X74481, or the RNA sequence complementary to such DNA sequence;

the virus-specific RNA probes targeted at HPV56 is a RNA sequence including the RNA sequence corresponding to the DNA sequences of 102-1567, 2432-3896, 5492-7096 of Genbank accession number X74483, or the RNA sequence complementary to such DNA sequence;

the virus-specific RNA probes targeted at HPV58 is a RNA sequence including the RNA sequence corresponding to the DNA sequences of 110-1542, 2763-4389, 5565-7139 of Genbank accession number D90400, or the RNA sequence complementary to such DNA sequence;

the virus-specific RNA probes targeted at HPV59 is a RNA sequence including the RNA sequence corresponding to the DNA sequences of 55-1398, 3567-4896, 5606-7132 of Genbank accession number X77858, or the RNA sequence complementary to such DNA sequence;

the virus-specific RNA probes targeted at HPV66 is a RNA sequence including the RNA sequence corresponding to the DNA sequences of 67-1534, 2679-4231, 5647-7158 of Genbank accession number U31794, or the RNA sequence complementary to such DNA sequence;

the virus-specific RNA probes targeted at HPV68 is a RNA sequence including the RNA sequence corresponding to the DNA sequences of 150-1678, 2986-4476, 5508-7025 of Genbank accession number FR751039, or the RNA sequence complementary to such DNA sequence;

In another preferred embodiment, the probes may be present separately or may be mixed in accordance with the detection requirement.

In another preferred embodiment, the kit comprises:

The probe reagent A: which comprises HPV16 and 18-type specific RNA probes;

The probe reagent B: which comprises HPV31, 33, 35, 39, 45, 51, 52, 56, 58, 59, 66, 68-type specific RNA probes; and Capture antibody, which is specific antibody against DNA-RNA heterozygote, wherein the antibody is contained in a solution or fixed on a solid-phase carrier;

The detection antibody, which is a specific antibody against DNA-RNA heterozygote linked with a detectable signal.

In another preferred embodiment, the solid phase carrier includes, but is not limited to: perforated plate, microsphere, test paper and slide.

In another preferred embodiment, the probe is with or without a marker (e.g. a fluorescent label)

In another preferred embodiment, the kit further comprises one or more reagents selected from the following groups:

High-risk HPV quality control product;
Low-risk HPV quality control product;
A washing liquid;
Denaturing liquid;
Reagent that identifies a detectable signal; and/or
A micro-pore plate;

Preferably, the detectable signal is selected from, but is not limited to, the following: alkaline phosphatase, horseradish peroxidase, glucose oxidase, beta-D-galactosidase, urease, catalase, or glucoamylase; the reagents for identifying the detectable signal are the substrates of alkaline phosphatase, horseradish peroxidase, glucose oxidase, beta-D-galactosidase, urease, catalase, or glucoamylase.

In another preferred embodiment, the high-risk HPV quality control product comprises:

The high-risk HPV low-value quality control product A: which is a solution containing 1 pg/ml HPV16 DNA; the high-risk HPV low-value quality control product B: which is a solution containing 1 pg/ml HPV58 DNA; the high-risk HPV high-value quality control product A: which is a 5 pg/ml HPV16 DNA solution; and a high-risk HPV high-value quality control substance B: a solution containing 5 pg/ml HPV58 DNA; or The low-risk type HPV quality control product is a solution containing 5 pg/ml HPV6 DNA.

In another aspect of the invention, the use of the kit is provided for high-risk HPV detection, wherein the high-risk HPV virus is of HPV16, 18, 31, 33, 35, 39, 45, 51, 52, 56, 58, 59, 66, 68 type-groups. In one preferred embodiment, the use is a non-disease diagnostic use.

In another aspect of the invention, the use of the kit is provided for typing high-risk HPV viruses, wherein the high-risk HPV viruses are classified into HPV16, 18-type groups, or HPV31, 33, 35, 39, 45, 51, 52, 56, 58, 59, 66 and 68-type groups. In one preferred embodiment, the use is a non-disease diagnostic use.

In another aspect of the invention, a high-risk HPV virus detection or typing method is provided, the method comprises the following steps: detecting a sample to-be-detected with the aforementioned kit; to judge the existence of the high risk type HPV16, 18, 31, 33, 35, 39, 45, 51, 52, 56, 58, 59, 66, 68 type groups; or The kit according to claim 3 is used for detecting a sample to-be-detected, to divide the high risk type HPV into HPV 16, 18 type groups or HPV31, 33, 35, 39, 45, 51, 52, 56, 58, 59, 66, 68 type groups.

In one preferred embodiment, the detecting or typing method comprises:

(1) Melting the DNA sample to be detected (preferably, further comprising the positive quality control product and the negative quality control product) into single chain (preferably, via denaturation melting), mixing with the probe reagent A and the probe reagent B respectively, to obtain hybridization solution A and hybridization solution B;

(2) Loading the hybridization solution A and the hybridization solution B respectively to solid-phase carrier A and solid-phase carrier B coated with capture antibody; forming a capture antibody and DNA-RNA heterozygote binary complex on the solid phase carrier A and the solid phase carrier B;

(2) Loading the detection antibody on a solid phase carrier, and forming ternary complex of capture antibody, DNA-RNA heterozygote and a detection antibody;

(3) Identifying the detectable signals on the solid-phase carriers A and B; determining whether a high-risk HPV virus exists in the sample to be detected; dividing the high risk type HPV into HPV 16, 18 type groups or HPV31, 33, 35, 39, 45, 51, 52, 56, 58, 59, 66, 68 type groups.

In another preferred embodiment, typing is as follows:

If the detectable signals on the solid-phase carriers A and B are both "positive", it indicates that the sample to-be-tested contains one or more of HPV31, 33, 35, 39, 45, 51, 52, 56, 58, 59, 66, 68, and also contains one or two of HPV16 and 18;

If only the detectable signal on the solid-phase carrier an is a "positive" signal, it indicates that the to-be-detected sample to be detected contains one or two of HPV16 and 18; and If only the detectable signal on the solid-phase carrier B is a "positive" signal, it indicates that the sample to-be-detected contains one or more of HPV31, 33, 35, 39, 45, 51, 52, 56, 58, 59, 66, 68.

In another preferred embodiment, the method is a non-disease diagnostic method, or the detection object directed to by the method (sample to be detected) is separated, including samples from public places or laboratory samples.

Other aspects of the invention will be apparent to those skilled in the art from the disclosure herein.

DETAILED EMBODIMENT OF THE INVENTION

Through deep research and extensive test, the inventors discloses probes with specific detection function for 14 HPV high-risk type viruses, and detection and typing technology for high-risk human papillomavirus (HPV) DNA based on the nucleic acid hybridization chemiluminescence immune technology Terms As used herein, "sample to-be-detected" or "nucleic acid (DNA) sample to-be-detected" refers to a nucleic acid sample to be detected, wherein it contains one kind of nucleic acid or a variety of nucleic acids, and it is necessary to know whether a target nucleic acid exists therein.

As used herein, "target nucleic acid" refers to a nucleic acid molecule of interest, for example, it is a marker or disease-related.

As used herein, a "DNA-RNA heterozygote" refers to a nucleic acid comprising two chains, wherein one chain is a DNA chain, and the other chain is a RNA chain, wherein the nucleotide sequence of the DNA chain and the nucleotide sequence of the RNA chain are substantially complementary. "Substantially complementary" means that the sequences of nucleotides are sufficiently complementary, and the interaction may occur in a predictable manner to form double strand. In general, two "substantially complementary" nucleotide sequences have at least 70% complementary nucleotides between each other; preferably, at least 80% nucleotides are complementary; more preferably, at least 90% nucleotides are complementary; further preferably, at least 95% nucleotides are complementary; such as 98%, 99%, or 100%.

As used herein, a "probe" refers to a single stranded nucleic acids of known nucleotide sequences (preferably RNA in the present invention) having a nucleotide sequence structure that is substantially complementary to the target nucleic acid, and can form a double strand with a "target nucleic acid". The "probe" may carry a marker or not. For example, a marker can be connected to the 5' end or the 3' end of the probe.

As used herein, a "capture antibody" refers to an antibody that can be coated on a solid phase carrier, and specifically recognize and bind to the DNA-RNA heterozygote but not bind to single stranded nucleic acids (including DNA or RNA, etc.) The "capture antibody" realizes the binding with a double-stranded hybrid by recognizing the double-helix structure of a double-stranded hybrid, rather than by base-sequence specificity. Coating an antibody on a solid phase carrier is common technology known by those skilled in the art. The term "capture antibody" can be used interchangeably with "coated antibody".

As used herein, a "detection antibody" refers to an antibody that specifically recognizes and binds to the DNA-RNA heterozygote, but not binds to single stranded nucleic acids (including DNA or RNA, etc.) The "detection antibody" realizes the binding with a double-stranded hybrid by recognizing the double-helix structure of a double-stranded hybrid, rather than by base-sequence specificity. The "detection antibody" carries a detectable signal for reporting the capture situation of the double stranded hybrid.

Kit

As is well known, HPV viruses have a very large variety of subtypes and variant strains, up to more than a hundred subtypes, wherein some of the subtype or variant are high-risk type, and some of the subtype or variant are low-risk type. Therefore, whether HPV virus exists in a sample to be detected and whether the HPV virus is high-risk type or not is crucial for clinical detection, prognosis, and the direction of medication scheme. However in view of the fact that the subtypes and the variant strains of HPV viruses are quite many and the homology of genome sequences between different strains is also very high, how to accurately and conveniently (best real-time) identify high-risk type HPV is always of high concern of the present art. At present, the clinically used method actually has a high proportion of false positive and false negative cases.

After long-term research, the inventors prepared a detection kit for specifically detecting 14 kinds of high-risk HPV viruses, the kit comprises RNA probes capable of specifically identifying 14 high-risk HPV viruses, which are obtained after being widely screened by the inventor and are appropriate in length and easy to synthesize artificially, with good specificity and will not cross-react with any other HPV types than the 14 high-risk types.

In the preferable mode of the invention, the probes are mixed in the kit. RNA probes specific against HPV types 16 and 18 are mixed to form probe reagent A; and the RNA probes specific against HPV types 31, 33, 35, 39, 45, 51, 52, 56, 58, 59, 66 and 68 are mixed to form a probe reagent formed. Therefore, the high-risk HPV viruses can be classified into HPV16, 18-type groups, or HPV31, 33, 35, 39, 45, 51, 52, 56, 58, 59, 66, and 68 type groups. Such arrangement can realize the discerning of HPV 16 and 18 type groups that causes 70% of female cervical cancer from other HPV viruses, which is very useful for clinical applications.

As other embodiments of the present invention, other high-risk HPV typing detection forms can be adopted. Adjusting specific HPV RNA probe components in the probe reagents, the 14 types of high-risk HPV can be typed by the 14 types, or by groups. For example, the current kit is divided into two groups: 2-type (HPV16, 18) and 12-type (HPV31, 33, 35, 39, 45, 51, 52, 56, 58, 59, 66, 68); or may also be divided into three groups: 1-type (HPV16), 1-type (HPV18) and 12-type (HPV31, 33, 35, 39, 45, 51, 52, 56, 58, 59, 66, 68), or other combinations may also be made. Of course, the group organization of 2-type (HPV16, 18) and 12-type (HPV31, 33 35, 39, 45, 51, 52, 56, 58, 66, 68) is most preferred.

As a preferred mode of the present invention, the probe reagents further comprises a certain concentration of salt ion components, such as trisodium citrate, sodium dihydrogen phosphate and the like besides the specific RNA probes, to ensure that the specific RNA probes and the single-stranded DNA can hybridize according to the complementary base pairing under a certain salt ion concentration.

Alternatively, the HPV RNA probes in the probe reagent may also carry a marker, such as biotin, digoxin antibody and tacrolimus; and the corresponding capture micro-pore plate is coated with biotin, digoxin antibody and tacrolimus-binding protein; or in the corresponding detection reagent there are avidin-labeled enzyme, digoxin antibody-labeled enzyme, and tacrolimus binding protein-labeled enzyme.

As a preferred mode of the present invention, the kit further comprises capture antibody and detection antibody.

The capture antibody and the detection antibody can be prepared by same antibody or different antibody, that is, the detection antibody can be the same or different from the capture antibody when not carrying a detectable signal. Using DNA-RNA heterozygote as antigen is different from using protein as an antigen. The antibody produced against DNA-RNA heterozygote has no specific sequence or antigen determinant requirements, and specifically recognizes the specific double-helix structure of the double-stranded hybrid. Anti-DNA-RNA antibody (whether monoclonal or polyclonal antibody) can bind to any DNA-RNA double-stranded hybrid. Method for preparing an antibody against double-stranded hybrid by using a specific double-stranded hybrid is known technology in the art, for example, polyclonal antibody can be prepared according to the method by Kitagawa& Stollar (Kitagawa Y, Stollar B D, Mol Immunol 1982, 19: 413-420); or monoclonal antibodies can be prepared according to the method by Fliss et al. (Fliss I, Laurent M, Emond E, et al., Appl Environ Microbiol, 1993, 59(8): 2698-2705).

As a preferred mode of the invention, the solution for detecting the antibody also contains NaCl, MgCl2 and Tween-20 in a certain concentration, to ensure that the non-specific adsorption of the detection antibody is reduced to the minimum when the detection antibody is combined with the DNA-RNA heterozygote in a solution containing a certain salt ion.

The solid-phase carrier adopted by the invention has no specific limitation, as long as the antibody can bind to the coating antibody (by coupling or linking). For example, the solid phase carrier is selected from a micro titration plate (such as a 96-well plate) slides, test paper, or microsphere. The technology for coating the antibody to solid phase carriers is also known to those skilled in the art.

The detectable signals are reporter molecule linked or coupled to detection antibodies for reporting the binding of the detection antibodies. Preferably, the detectable signal is selected from alkaline phosphatase (AP), horse radish peroxidase (HRP), glucose oxidase, beta-D-galactosidase, urease, catalase, or glucoamylase. These detectable signals have particular substrates, and a chromogenic reaction or other reactions that can be detected or be visible after being in contact with the substrate may occur, thus, the binding of the detection antibody is reported. The substrate comprises, for example, o-phenylenediamine, tetramethyl benzidine (TMB), ABTS for horseradish peroxidase (OPD); p-nitrophenyl phosphate (p-NPP) for alkaline phosphatase, CDP-Star; etc.

As a preferred mode of the invention, the kit can further comprise a negative quality control product (NC), low-risk and high-risk HPV quality control products (including, such as high-risk HPV low-value quality control product A (HLC-A), the high-risk HPV low-value quality control product B (HLC-B), the high-risk HPV high-value quality control product A (HHC-A), and high-risk HPV high-value quality control product B (HHC-B), and low-risk HPV quality control product (LC).

In order to facilitate operation, the kit can also comprise the reagents required by the operations such as nucleic acid melting, washing, developing and the like. Reagents for melting treatment are such as denaturing reagents (e.g., alkali treatment reagents), and reagents for developing treatment are such as indicator dyes.

As a preferable mode of the invention, the kit further comprises a sample preservation solution, whose main components are TE buffer solution containing a certain concentration of salt, to stably store the nucleic acid in the TE buffer solution.

As a preferable mode of the invention, the washing solution is a buffer solution with a certain pH value, for reducing non-specific adsorption.

The detection kit provided by the invention is high in specificity, high in sensitivity and low in cost, wherein no DNA amplification or special test conditions are needed, the operation is simple and easy for training, and the experimental pollution is reduced to the minimum. Two high-risk HPV types (HPV16, 18) and 12 high-risk HPV (HPV31, 33, 35, 39, 45, 51, 52, 56, 58, 59, 66, 68) among the 14 high-risk HPV types can be typed and detected.

In addition, the kit can further comprise the application description and the like.

Detection Method

Figure 1:
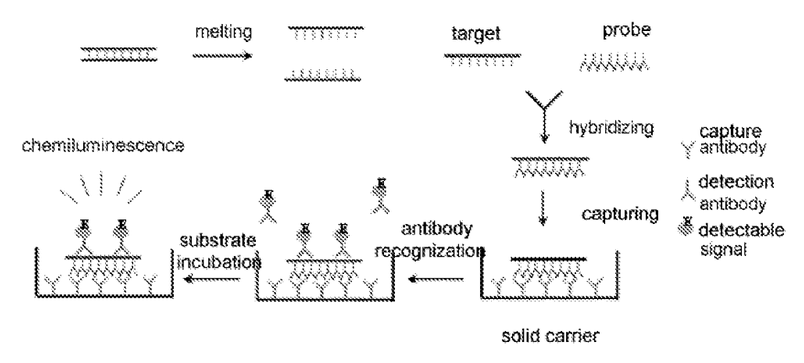
FIG. 1 is a schematic diagram of the detection principle of the present method of the invention.

The present method is based on the ELISA reaction principle. However, in the method designed by the inventor, the object captured by the antibody is special, that is, the DNA-RNA heterozygote formed by DNA and RNA complementation, rather than conventional protein. The particular principle (FIG. 1) is: the HPV double-stranded DNA in the sample is denatured into single-strand, the single-stranded DNA bind with specific RNA probe to form DNA-RNA heterozygote, the DNA-RNA heterozygote is associated with capture antibody on a solid phase carrier (such as a micro-pore plate) that is coated with a capture antibody, and then bind to a detection antibody coupled with a detectable signal; by detecting the detectable signal, HPV viral nucleic acids in a sample are qualitatively detected, and typing is realized.

As a preferred mode of the invention, after hybridization, the hybridization solution is transferred to a solid phase carrier and shaken for reaction. Because the hybridization solution contains a certain concentration of salt brought in by the sample preservation solution and of the rapid shaking reaction, the specific high-affinity monoclonal antibody coated on the DNA-RNA heterozygote capture microporous plate can capture as much as possible for more than 90% of the paired DNA-RNA heterozygote in the hybridization solution.

As the preferred mode of the invention, the method of the present invention provides typing technology for two high-risk HPV (HPV16, 18) that cause 70% of cervical cancer, overcoming the defect in the existing detection technology which is insufficient in high-risk HPV typing. Other combinations may be performed according to the need of detection. Of course, the group mode of 2-type (HPV16, and 18) and 12-type (HPV31, 33, 35, 39, 45, 51, 52, 56, 58, 59, 66, 68) is most preferred. The inventors have found that the detection effect of such combination is very ideal, and almost does not have the possibility of cross reaction with other viruses.

The method of the invention does not need PCR technology with high requirements for laboratory environment, overcomes the defects in the PCR technology that the experiment pollution is not easy to control, the false negative is high, the presence of competitive inhibition exists, and the influence caused by sample preservation and DNA extraction process and the like.

The embodiments of the present invention are further described below with reference to specific examples. It should be understood that these embodiments are for illustrative purposes only and are not intended to limit the scope of the invention. The experimental method not noted with the specific conditions in the following examples is usually according to conventional conditions, such as Sambrook et al, Molecular Cloning, A Laboratory Mannual, 3rd edition, Cold Spring Harbor Laboratory, 2002, or the conditions suggested by the manufacturer.

Example 1 Preparation of Probe Reagents and Quality Control Products

1. Preparation of Probe Reagent a and Probe Reagent B
The preparation method is as follows:
(1) Firstly, synthesizing the following DNA sequence fragments (SEQ ID NO: 1):

```
  Kpn I      T7promoter       Nhe I       Not I    Xba I
GAGGGTACC TAATACGACTCACTATAG GGCTAGC AAA GCGGCCGC TCTAGAGAC
```

(2) Cloning the above synthesized DNA sequence into Kpn I and Xba I site of a pUC19 carrier, thereby obtaining the modified pUC19 vector.
(3) Respectively, synthesizing genomic DNA fragments of HPV16, 18, 31, 33, 35, 39, 45, 51, 52, 56, 58, 59, 66, 68 subtypes, and the sequence fragments of each DNA are respectively:
HPV16: the 83-1558, 3193-4628, 5559-7154 sites in the sequence of Genbank accession no. K02718;
HPV18: the 105-1593, 2376-3867, 5430-7136 sites in the sequence of the Genbank accession number X5015;
HPV31: the 108-1463, 3564-4982 and 5558-7072 sites in the sequence of Genbank accession no. HQ537666;
HPV33: the 109-1654, 3789-5087, 5594-7093 sites in the sequence of Genbank accession no. M12732;
HPV35: the 110-1476, 3452-4897, 5601-7109 sites in the sequence of Genbank accession no. X74477;
HPV39: the 107-1608, 2654-4187 and 5643-7160 sites in the sequence of the Genbank accession no. M62849;
HPV45: the 102-1543, 3421-4872, and 5530-7149 sites in the sequence of Genbank accession no. X74479;
HPV51: the 68-1476, 2875-4452 and 5894-7431 sites in the sequence of the Genbank accession number M62877;
HPV52: the 89-1565, 2459-4098, 5565-7154 sites in the sequence of Genbank accession no. X74481;
HPV56: the 102-1567, 2432-3896 and 5492-7096 sites in the sequence of the accession number X74483;
HPV58: the 110-1542, 2763-4389, 5565-7139 sites in the sequence of the Genbank accession number D90400;
HPV59: the 55-1398, 3567-4896 and 5606-7132 sites in the sequence of the Genbank accession number X77858;
HPV66: the 67-1534, 2679-4231, 5647-7158 sites in the sequence of the Genbank accession number U31794;
HPV68: the 150-1678, 2986-4476, and 5508-7025 sites in the sequence of Genbank accession no. FR751039; and
In addition, a sequence of NheI site (GCTAGC) is added to the 5'-end of the above sequence, and a sequence of NotI site (GCGCCGC) is added to the 3' end.
(4) Respectively, cloning the above synthesized DNA sequences into the NheI/NotI site of the modified pUC19 vector.

The upstream of the above DNA sequences was connected with T7 respectively, and the constructed vector was used as a template (template DNA). After NotI enzyme digestion, T7 RNA polymerase was used to prepare the RNA probes for HPV16, 18, 31, 33, 35, 39, 45, 51, 52, 56, 58, 59, 66, 68. The reaction conditions for preparing RNA by T7 RNA polymerase: 10 µL 5×transcriptional buffer, 10 µL 10 mM 4NTP (ATP, CTP, GTP, UTP) mixed solution, 1 µg template DNA, 50 U RNA enzyme inhibitor, 1.5 µL T7 RNA polymerase (20 U/µL); DEPC-treated water was added to a total volume of 50 µl; and the mixed solution was preserved at 37° C. for 100 minutes, 2 µL of 0.5M EDTA was added to terminate the reaction.

(6) Mixing the HPV16 and the HPV18 RNA probes to obtain probe reagent A, namely, a solution containing HPV16 and 18 RNA probes; the concentration of the HPV16 RNA probe is 0.5 µg/ml, and the concentration of the HPV18 RNA probe is 0.5 µg/ml. The solution further comprises: 0.125M trisodium citrate, 0.125M sodium dihydrogen phosphate.
(7) Mixing the other probes except the HPV16 and the HPV18 RNA probes to obtain a probe reagent B, namely the solution comprising the RNA probes for HPV31, 33, 35, 39, 45, 51, 52, 56, 58, 59, 66, and 68. In the solution, the concentration of each RNA probe is 0.5 µg/ml. The solution further comprises: 0.125M trisodium citrate, 0.125M sodium dihydrogen phosphate.

2. Preparation of Quality Control Products
Preparing the quality control products comprising HPV6 DNA, HPV16 DNA and HPV58 DNA, as follows:
(1) Synthesizing the HPV6 (1-8031 sites in the sequence of the Genbank accession number FR 751337), HPV16 (1-7904 sites in the sequence of the Genbank accession no. K02718), HPV58 (1-7824 sites in the sequence of Genbank accession no. D90400) by chemical synthesis method, and add Kpn I and Xba I to both ends.
(2) Cloning the above sequences into the Kpn I and Xba I sites of a pUC18 vector respectively, to construct HPV plasmid;
(3) Transforming the HPV plasmids into E. coli DH5α;
(4) Selecting a monoclonal bacterial strain on a solid agar culture plate containing ampicillin resistance;
(5) Expanding and culturing the monoclonal strain in LB culture medium;
(6) Extracting plasmid DNA, and carrying out identification and quantitative analysis. The obtained recombinant plasmid DNA can be used as a quality control product. In the low-risk HPV quality control products, the concentration of the HPV6 DNA plasmid is 5 pg/ml; in the high-risk HPV high-value quality control product, the concentration of HPV16 DNA plasmid is 5 pg/ml, the concentration of the HPV58 DNA plasmids is 5 pg/ml; in a high-risk HPV low-value quality control product, the concentration of HPV16 DNA plasmids is 1 pg/ml, and the concentration of the HPV58 DNA plasmids is 1 pg/ml which are all independently placed in each quality control product tube. The quality control product dilution solution further comprises: 10 mM tris, 10 mM EDTA, at pH 7.2±0.2.

Example 2 Kit Assembling

Kit 1:
The probe reagent A and the probe reagent B prepared in Example 1 are packed in the kit to obtain the detection reagent kit 1.
Kit 2:
The probe reagent A, the probe reagent B and the quality control products prepared in Example 1 are placed in different containers respectively, loaded in the kit and further packed in the kit. The kit is further packed with:
Coated antibody: ATCC # HB-8730, dissolved in carbonate buffer (pH9.6) and can be used for coating micro-pore plates.
Detection antibody: Solution of high specific antibody against DNA-RNA heterozygote, coupled with alkaline phosphatase (ATCC # HB-8730) (antibody concentration: 100 ng/ml). The solution further contains 0.6M NaCl, 0.1 mg $MgCl_2$, 0.25% Tween –20.

A detection reagent kit 2 is obtained.

Kit 3:

On the basis of the kit 1, the following reagents (reagents are respectively packed in independent containers) are further included:

1. Denaturing reagent (denaturing liquid): a solution containing 1.75 M sodium hydroxide.

2. Capture micro-pore plate: for coating a chemiluminescence plate with a specific antibody against DNA-RNA heterozygote, coating a 96-well plate with coating antibody (ATCC#HB8730, dissolved in a carbonate buffer (pH9.6)) at 0.1 µg/ml, 100 µl/well.

3. Detection reagent: Solution of high specific antibody against DNA-RNA heterozygote, coupled with alkaline phosphatase (ATCC # HB 8730) (antibody concentration: 100 ng/ml). The solution further contains 0.6M NaCl, 0.1 mg $MgCl_2$, 0.25% Tween –20.

4. The substrate reagent: alkaline phosphatase chemiluminescent substrate, and is 0.4 mM CDP-star solution.

5. 10× concentrated washing solution is 10*TBS buffer solution.

6. Negative quality control product (NC): sample preservation solution (10 mM Tris, 10 mM EDTA, pH 7.2±0.2);

7. High-risk type HPV low-value quality control product A (HLC-A) is a solution containing 1 pg/ml HPV16 DNA.

8. High-risk type HPV low-value quality control product B (HLC-B) is a solution containing 1 pg/ml HPV58 DNA.

9. High-risk type HPV high-value quality control product A (HHC-A) is a solution containing 5 pg/ml HPV16 DNA.

10. High-risk type HPV high-value quality control product B (HHC-B) is a solution containing 5 pg/ml HPV58 DNA.

11. Low-risk type HPV quality control product (LC) is a solution containing 5 pg/ml HPV6 DNA.

Example 3 Typing Detection of HPV DNA

Using the kit 3 in example 2 to perform typing detection on the HPV DNA, as follows:

Denaturation: 0.5 ml denaturing reagent was added into the storage tube of the sample to be detected (1 ml) and each quality control product (1 ML) tube, incubating for 45 minutes in a 65° C. water bath to degrade RNA in the sample, and denature the double-stranded DNA into single-stranded DNA.

Hybridization: preparing two 96-well microtiter plates, one was labeled as "hybrid micro-pore plate A", and the other was labeled as "hybrid micro-pore plate B". probe reagent A (25 µL/well) was added into the hybridization micro-pore plate A and probe reagent B (25 µL/well) was added into the hybrid micro-pore plate B; taking out the denatured quality control products and the sample to be detected from the water bath, and recovering to room temperature; 75 µl of each was added into the hybrid micro-pore plates A and B respectively; sealing the hybrid micro-pore plate by using a plate-sealing film; placing the hybrid micro-pore plates on a micro-pore plate heating agitator, agitating at 1000 rpm for 3 min; stopping agitation and incubating at 65° c. for 60 minutes, taking out the hybrid micro-pore plate A and the hybrid micro-pore plate B from the micro-pore plate heating agitator, and cooling to room temperature.

Capturing: preparing two 96-well microtiter plates, one was labeled as "capture micro-pore plate A", and the other was labeled as "capture micro-pore plate B", Completely transferring the liquid in the hybrid micro-pore plate (about 100 µl/well) into the corresponding well in the capture micro-pore plate; sealing the capture micro-pore plate by a plate-sealing film; putting onto a micro-pore plate heating agitator that has cooled to room temperature, agitating at 1100 rpm for 60 minutes at room temperature.

Detection: taking out the captured micro-pore plate, and removing the liquid in the capture micro-pore plate (about 100 µl/well); and adding a detection reagent (75 µl/well) into the capture micropore plate, incubating at room temperature for 45-60 minutes.

Chemiluminescence: Removing the detection reagent (about 75 µl/well) in the capture micro-pore plate, washing the capture micro-pore plate with 1*washing solution, adding substrate reagent (75 µl/well) into the capture micro-pore plate, incubating for 15-30 minutes at room temperature in dark, and reading on a chemiluminescence immunoassay analyzer.

Reference Values:

The determination of the effectiveness of the detection is used to determine whether the reagent and the operation are effective or not, whether the detection reference value can be given accurately, and the detection effectiveness must be determined for each detection.

When the mean value of the high-risk HPV low-value quality control products/the mean value of the negative quality control products ≥2.0, the detection is effective, and the mean value of the high-risk HPV low-value quality control product is the reference value for this detection. All the detections are indicated by the ratio of sample measurement value/reference value (S/Cutoff)), wherein the ratio is ≥1.0 means that the result is positive, and when the ratio is <1.0, the result is "negative".

The test result is determined as follows:

1. Two groups of micro-pore plates are used to respectively detect two (HPV16, and 18 type) and 12 (HPV31, 33, 35, 39, 45, 51, 52, 56, 58, 59, 66, 68 type) high-risk human papillomavirus (HPV) nucleic acid.

2. When the detection results of the capture micro-pore plate A and the capture micro-pore plate B are both "positive", it indicates that the sample contains both one or two of the 2-type (HPV16, 18-type) high-risk human papillomavirus and one or more of the 12-type (HPV31, 33, 35, 39, 45, 35, 39, 45, 51, 52, 56, 58, 59, 66, 68) high-risk human papilloma virus.

3. When the detection result of the capture micro-pore plate A is "positive" and result of the capture micro-pore plate B is "negative", it indicates that the sample contains one or two of the 2-type (HPV16, 18-type) high-risk human papillomavirus.

4. When the detection result of the capture micro-pore plate A is "negative" and the result of the capture micro-pore plate B is "positive", it indicates that the sample contains one or more of the 12-type (HPV31, 33, 35, 39, 45, 35, 39, 45, 51, 52, 56, 58, 59, 66, 68) high-risk human papilloma virus.

Example 4 Study of the Lowest Detection Limit and Cross-Reactivity

1. Study of the Lowest Detection Limit

The probe reagent A in the kit 3 of example 2 is used for carrying out the lowest detection limit study on HPV16 and 18 DNA, the ratio S/N of different HPV DNA concentration measurement values and zero concentration measurement values is made, and the detail method is as follows: different concentrations (0.5 pg/ml, 1 pg/ml, 2 pg/mL, 5 pg/mL, 10 pg/mL, 50 pg/mL, 100 pg/mL dissolved in a sample preservation solution (10 mM Tris, 10 mM EDTA, pH 7.2±0.2)) of HPV 16 and 18 DNAs are subjected to detection by the probe reagent A in the kit and denaturation, hybridization, capture and detection steps in the detection process are the same as that in Example 3.

The results are shown in table 2 and table 3.

TABLE 2

| HPV16 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.08 | 4.48 | 9.08 | 22.11 | 44.75 | 289.00 | 580.26 |

TABLE 3

| HPV18 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.08 | 4.47 | 9.67 | 24.04 | 47.06 | 300.44 | 588.96 |

As can be seen from table 2 and table 3, the lowest detection limits of both the HPV16 and 18 DNA are 0.5 pg/ml which indicates that the kit provided by the invention can be used for detecting viruses in samples with extremely low-concentration, and is very ideal in sensitivity.

The probe reagent B in the kit 3 of Example 2 is used for carrying out the lowest detection limit study on HPV31, 33, 35, 39, 45, 51, 52, 56, 58, 59, 66 and 68 DNA, the ratio S/N of different HPV DNA concentration measurement values and zero concentration measurement values is made, and the detail method is as follows: different concentrations (0.5 pg/ml, 1 pg/ml, 2 pg/mL, 5 pg/mL, 10 pg/mL, 50 pg/mL, 100 pg/mL; dissolved in a sample preservation solution (10 mM Tris, 10 mM EDTA, pH 7.2±0.2)) of HPV 31, 33, 35, 39, 45, 51, 52, 56, 58, 59, 66 and 68 DNAs are subjected to detection by the probe reagent B in the kit and denaturation, hybridization, capture and detection steps in the detection process are the same as that in Example 3.

The results are shown in Tables 4-15.

TABLE 4

| HPV31 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.19 | 4.19 | 8.76 | 21.26 | 42.48 | 203.39 | 406.51 |

TABLE 5

| HPV33 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.18 | 4.20 | 8.22 | 20.68 | 42.17 | 203.39 | 393.10 |

TABLE 6

| HPV35 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.31 | 4.45 | 8.81 | 20.95 | 42.87 | 212.32 | 402.34 |

TABLE 7

| HPV39 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.18 | 4.24 | 8.46 | 20.78 | 42.52 | 207.76 | 408.62 |

TABLE 8

| HPV45 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.03 | 3.99 | 7.88 | 19.31 | 37.21 | 190.88 | 360.75 |

TABLE 9

| HPV51 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.07 | 4.03 | 7.78 | 19.58 | 37.90 | 190.88 | 373.96 |

TABLE 10

| HPV52 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.03 | 3.66 | 7.80 | 19.03 | 37.88 | 195.97 | 368.83 |

TABLE 11

| HPV56 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.03 | 3.87 | 7.91 | 18.88 | 37.62 | 198.44 | 371.01 |

TABLE 12

| HPV58 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.12 | 4.20 | 8.44 | 21.62 | 42.38 | 213.81 | 415.44 |

TABLE 13

| HPV59 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.13 | 4.26 | 8.62 | 23.07 | 41.84 | 218.42 | 412.26 |

TABLE 14

| HPV66 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.15 | 4.19 | 8.54 | 23.39 | 41.32 | 227.49 | 400.69 |

TABLE 15

| HPV68 DNA | 0.5 pg/ml | 1 pg/ml | 2 pg/ml | 5 pg/ml | 10 pg/ml | 50 pg/ml | 100 pg/ml |
|---|---|---|---|---|---|---|---|
| S/N | 2.11 | 4.20 | 8.57 | 23.01 | 40.61 | 228.68 | 399.92 |

As can be seen from tables 4-15, the lowest detection limits of HPV31, 33, 35, 39, 45, 51, 52, 56, 58, 59, 66 DNAs are all 0.5 pg/ml which indicates that the kit provided by the invention can be used for detecting viruses in samples with extremely low-concentration, and is very ideal in sensitivity.

2. Cross-Reactive Study

Cross-reaction research is carried out on the kit 3 in example 2. The probe reagent A is used for the cross-reaction study with CT (*Chlamydia Trachomatis*), NG (*Neissera Gonorrhoeae*), UU (*Ureapramaurealyticum, mycoplasma-M. urealyticum*), CMV (human cytomegalovirus), HSV (human simplex virus), and other types of HPVs besides two HPVs (HPV 16 and 18) (HPV 6, 11, 26, 31, 33, 35, 39, 51, 52, 56, 58, 59, 61, 66, 67, 68, 69, 71, 73, 81). On the basis of effective detection, the ratio of the measurement value/reference value of each well is calculated; The probe reagent B is used for the cross-reaction study with CT, NG, UU, CMV, HSV, and other types of HPVs (HPV 6, 11, 16, 26, 61, 67, 69, 71, 73, 81) besides 12 HPVs (HPV 31, 33, 35, 39, 45, 51, 52, 56, 58, 59, 66, 68). The steps of denaturation, hybridization, capture and detection in the detection process are the same as those in Example 3.

In the above method, various samples to be studied for cross reaction were dissolved in a sample preservation solution at 25 pg/ml (10 mmol/1 Tris, 10 mM EDTA, pH 7.2±0.2). On the basis of effective detection, the ratio of the measurement value/reference value (S/Cutoff) of each well is calculated; the ratio ≥1 indicates the presence of cross-reaction; the ration <1 indicates no cross-reaction.

The detection data is shown in tables 16 and 17.

TABLE 16

Cross reaction study of probe reagent A in the kit

| Sample to be detected | Batch1 S/Cutoff, result | Batch2 S/Cutoff, result | Batch3 S/Cutoff, result |
|---|---|---|---|
| CT | 0.24, negative | 0.25, negative | 0.23, negative |
| NG | 0.25, negative | 0.24, negative | 0.26, negative |
| UU | 0.24, negative | 0.23, negative | 0.25, negative |
| CMV | 0.23, negative | 0.24, negative | 0.23, negative |
| HSV | 0.24, negative | 0.25, negative | 0.23, negative |
| HPV6 | 0.27, negative | 0.28, negative | 0.26, negative |
| HPV11 | 0.29, negative | 0.28, negative | 0.28, negative |
| HPV26 | 0.25, negative | 0.26, negative | 0.27, negative |
| HPV31 | 0.33, negative | 0.34, negative | 0.35, negative |
| HPV33 | 0.32, negative | 0.33, negative | 0.34, negative |
| HPV35 | 0.41, negative | 0.42, negative | 0.42, negative |
| HPV39 | 0.29, negative | 0.30, negative | 0.28, negative |
| HPV51 | 0.24, negative | 0.25, negative | 0.23, negative |
| HPV52 | 0.27, negative | 0.26, negative | 0.26, negative |
| HPV56 | 0.23, negative | 0.23, negative | 0.24, negative |
| HPV58 | 0.32, negative | 0.31, negative | 0.31, negative |
| HPV59 | 0.28, negative | 0.27, negative | 0.29, negative |
| HPV61 | 0.24, negative | 0.26, negative | 0.25, negative |
| HPV66 | 0.25, negative | 0.25, negative | 0.24, negative |
| HPV67 | 0.23, negative | 0.24, negative | 0.24, negative |
| HPV68 | 0.27, negative | 0.26, negative | 0.26, negative |
| HPV69 | 0.23, negative | 0.24, negative | 0.23, negative |
| HPV71 | 0.23, negative | 0.24, negative | 0.24, negative |
| HPV73 | 0.25, negative | 0.23, negative | 0.24, negative |
| HPV81 | 0.23, negative | 0.23, negative | 0.24, negative |

TABLE 17

Cross reaction study of probe reagent B in the kit

| Sample to be detected | Batch1 S/Cutoff, result | Batch2 S/Cutoff, result | Batch3 S/Cutoff, result |
|---|---|---|---|
| CT | 0.23, negative | 0.25, negative | 0.24, negative |
| NG | 0.24, negative | 0.23, negative | 0.24, negative |
| UU | 0.24, negative | 0.24, negative | 0.25, negative |
| CMV | 0.23, negative | 0.24, negative | 0.23, negative |
| HSV | 0.24, negative | 0.23, negative | 0.25, negative |
| HPV6 | 0.24, negative | 0.25, negative | 0.25, negative |
| HPV11 | 0.25, negative | 0.26, negative | 0.25, negative |
| HPV16 | 0.27, negative | 0.28, negative | 0.27, negative |
| HPV26 | 0.24, negative | 0.24, negative | 0.23, negative |
| HPV61 | 0.23, negative | 0.24, negative | 0.25, negative |
| HPV67 | 0.29, negative | 0.30, negative | 0.31, negative |
| HPV69 | 0.29, negative | 0.28, negative | 0.27, negative |
| HPV71 | 0.24, negative | 0.23, negative | 0.24, negative |
| HPV73 | 0.23, negative | 0.24, negative | 0.24, negative |
| HPV81 | 0.24, negative | 0.24, negative | 0.25, negative |

According to the above result analysis: Analysis of the cross reaction study results of three lots of kits, both the ratio of measurement value to reference value (S/Cutoff) for each well of the capture micropore plate A and the capture micro-pore plate B are <1.0, and the test results are both negative, indicating that the probe A of the present kit has no cross-reactivity to CT, NG, UU, CMV, HSV, and other types of HPVs (HPV6, 11, 26, 31, 33, 35, 39, 51, 52, 56, 58, 59, 61, 66, 67, 68, 69, 71, 73, 81) besides 2 HPV (HPV16, 18); and the probe B of the present kit has no cross-reactivity to CT, NG, UU, CMV, HSV and other types of HPVs (HPV6, 11, 16, 26, 61, 67, 69, 71, 73, 81) besides 12 HPVs (HPV 31, 33, 35, 39, 45, 51, 52, 56, 58, 59, 66, 68).

Example 5 Detection of Clinical Cervical Exfoliated Cell Samples

1. Detection of 8 Clinical Samples

Collecting the sample to-be-tested: samples are collected by collecting the cervical exfoliated cell sample of the clinical patients from the maternity hospital of the medical college of zhejiang university. After cervical exfoliated cell samples were collected by gynecologist using common method, the samples were placed into sample preservation tubes containing 1 ml of sample preservation solution, and numbered as 1-8.

The reagents used are the same as the kit 3 in example 2, and the cervical foliated cell samples were detected. The detection steps and the determination of the results are the same as in Example 3. Particular detection results are shown as in Table 18.

TABLE 18

| Sample number | Test result of the present kit | Test result of final diagnosis from the hospital | Result consistency |
|---|---|---|---|
| 1 | 2-type: 0.25, negative<br>12-type: 18.41, positive | positive | consistent |
| 2 | 2-type: 0.26, negative<br>12-type: 0.25, negative | negative | consistent |
| 3 | 2-type: 25.37, positive<br>12-type: 38.21, positive | positive | consistent |
| 4 | 2-type: 7.46, positive<br>12-type: 0.23, negative | positive | consistent |

TABLE 18-continued

| Sample number | Test result of the present kit | Test result of final diagnosis from the hospital | Result consistency |
|---|---|---|---|
| 5 | 2-type: 0.76, negative<br>12-type: 0.24, negative | negative | consistent |
| 6 | 2-type: 0.28, negative<br>12-type: 69.73, positive | positive | consistent |
| 7 | 2-type: 0.23, negative<br>12-type: 2.26, positive | positive | consistent |
| 8 | 2-type: 0.26, negative<br>12-type: 0.35, negative | negative | consistent |

Wherein, the 2-type represents: at least one of HPV16 or HPV18 type;

Wherein, the 12-type represents: at least one of HPV31, 33, 35, 39, 45, 51, 52, 56, 58, 59, 66, 68.

As can be seen from the results of table 18 above, the result of the kit of the present invention is completely consistent with the final diagnosis of the hospital, which indicates good specificity and preciseness. Furthermore, the kit provided by the invention can also realize typing detection for 2 types of high-risk HPVs (HPV 16, 18) and 12 types of high-risk HPV (HPV 31, 33, 35, 39, 45, 51, 52, 56, 58, 59, 66, 68) in the 14 high risk HPVs.

2. Statistics of the Detection Data of More Clinical Samples

For 1404 cases of the cervical foliated cell samples of the patients collected from the maternity hospital of the medical college of Zhejiang university, Qilu hospital of Shandong University, and 1st hospital of Wenzhou medical college, the inventor used same detection as in "1" of the present example, and analyzed the detection result data. The results are shown in table 19.

TABLE 19

| Test result diagnosed by the hospital | Test products (2 + 12type) Positive | Negative | Total | Kappa Factor (95% CI) |
|---|---|---|---|---|
| Positive | 971 | 13 | 984 | 0.9662 |
| Negative | 7 | 413 | 420 | (95.14%~98.09%) |
| total | 978 | 426 | 1404 | |
| Positive consistency and the 95% CI | | 98.68%(97.75%~99.29%) | | |
| negative consistency and the 95% CI | | 98.33%(96.60%~99.33%) | | |

TABLE 19-continued

| Test result diagnosed by the hospital | Test products (2 + 12type) Positive | Negative | Total | Kappa Factor (95% CI) |
|---|---|---|---|---|
| total consistency and the 95% CI | | 98.58%(97.81%~99.13%) | | |

As can be seen from table 19, the kappa coefficient is 0.9662 and 95% CI is 95.14%-98.09%, comparing to the results of the final diagnosis of the hospital, thus having good consistency. The positive consistency percentage is 98.68%, and the negative consistency percentage is 98.33%, and the total consistency rate is 98.58%. Comprehensive analysis shows that the present test product has high consistency with the determination result of the final diagnosis of the hospitals.

The invention claimed is:

1. A kit for high-risk HPV detection, wherein the kit comprises:
   a probe reagent A: which comprises HPV16 and 18-type specific RNA probes; and
   a probe reagent B: which comprises HPV31, 33, 35, 39, 45, 51, 52, 56, 58, 59, 66, and 68-type specific RNA probes;
   wherein the HPV16-type specific RNA probes consist of sequences complementary to the DNA sequences 83-1558, 3193-4628 and 5559-7154 of Genbank accession number k02718;
   wherein the HPV18-type specific RNA probes consist of sequences complementary to the DNA sequences 105-1593, 2376-3867 and 5430-7136 of Genbank accession number X05015;
   wherein the HPV31-type specific RNA probes consist of sequences complementary to the DNA sequences 108-1463, 3564-4982 and 5558-7072 of Genbank accession number HQ537666;
   wherein the HPV33-type specific RNA probes consist of sequences complementary to the DNA sequences 109-1654, 3789-5087 and 5594-7093 of Genbank accession number M12732;
   wherein the HPV35-type specific RNA probes consist of sequences complementary to the DNA sequences 110-1476, 3452-4897 and 5601-7109 of Genbank accession number X74477;

wherein the HPV39-type specific RNA probes consist of sequences complementary to the DNA sequences 107-1608, 2654-4187 and 5643-7160 of Genbank accession number M62849;

wherein the HPV45-type specific RNA probes consist of sequences complementary to the DNA sequences 102-1543, 3421-4872 and 5530-7149 of Genbank accession number X74479;

wherein the HPV51-type specific RNA probes consist of sequences complementary to the DNA sequences 68-1476, 2875-4452 and 5894-7431 of Genbank accession number M62877;

wherein the HPV52-type specific RNA probes consist of sequences complementary to the DNA sequences 89-1565, 2459-4098 and 5565-7154 of Genbank accession number X74481;

wherein the HPV56-type specific RNA probes consist of sequences complementary to the DNA sequences 102-1567, 2432-3896 and 5492-7096 of Genbank accession number X74483;

wherein the HPV58-type specific RNA probes consist of sequences complementary to the DNA sequences 110-1542, 2763-4389 and 5565-7139 of Genbank accession number D90400;

wherein the HPV59-type specific RNA probes consist of sequences complementary to the DNA sequences 55-1398, 3567-4896 and 5606-7132 of Genbank accession number X77858;

wherein the HPV66-type specific RNA probes consist of sequences complementary to the DNA sequences 67-1534, 2679-4231 and 5647-7158 of Genbank accession number U31794;

wherein the HPV68-type specific RNA probes consist of sequences complementary to the DNA sequences 150-1678, 2986-4476 and 5508-7025 of Genbank accession number FR751039.

2. The kit according to claim 1, wherein the kit comprises: a probe reagent A, which comprises HPV16- and HPV18-type specific RNA probes; and a probe reagent B, which comprises HPV31, 33, 35, 39, 45, 51, 52, 56, 58, 59, 66, 68-type specific RNA probes, and wherein the kit further comprises: a capture antibody, which is a specific antibody against DNA-RNA heterozygote, wherein said antibody is contained in a solution or fixed on a solid-phase carrier; and a detection antibody, which is a specific antibody against DNA-RNA heterozygote, and is linked with a detectable signal.

3. The kit according to claim 1, wherein the kit further comprises one or more reagents selected from the following groups:

High-risk HPV quality control product;

Low-risk HPV quality control product;

A washing liquid;

Denaturing liquid;

Reagent that identifies a detectable signal; and/or

A micro-pore plate.

4. A detecting method for high-risk HPV, wherein the method comprises the following steps: detecting a sample to-be-detected with the kit according to claim 1 to judge the existence of high risk type HPV16, 18, 31, 33, 35, 39, 45, 51, 52, 56, 58, 59, 66, 68.

5. A detecting or typing method for high-risk HPV, wherein the method comprises the following steps: detecting a sample to-be-detected with the kit according to claim 2, to divide the high risk type HPV into HPV 16,18 type groups or HPV31, 33, 35, 39, 45, 51, 52, 56, 58, 59, 66, 68 type groups.

6. The method according to claim 5, wherein the detecting or typing method comprises:

(1) Melting the DNA sample to be detected into single chain, mixing with the probe reagent A and the probe reagent B separately, to obtain a hybridization solution A and a hybridization solution B;

(2) Loading the hybridization solution A and the hybridization solution B respectively to a solid-phase carrier A and a solid-phase carrier B coated with capture antibody; forming a capture antibody and DNA-RNA heterozygote binary complex on the solid phase carrier A and the solid phase carrier B;

(3) Loading the detection antibody on a solid phase carrier, and forming ternary complex of capture antibody, DNA-RNA heterozygote and a detection antibody;

(4) Identifying the detectable signals on the solid-phase carriers A and B; and determining whether a high-risk HPV virus exists in the sample to be detected; dividing the high risk type HPV into HPV 16,18 type groups or HPV31, 33, 35, 39, 45, 51, 52, 56, 58, 59, 66, 68 type groups.

7. The kit according to claim 3, wherein the said detectable signal is selected from: alkaline phosphatase, horseradish peroxidase, glucose oxidase, beta-D-galactosidase, urease, catalase, or glucoamylase; the reagents for identifying the detectable signal are the substrates of alkaline phosphatase, horseradish peroxidase, glucose oxidase, beta-D-galactosidase, urease, catalase, or glucoamylase.

* * * * *

```
SEQUENCE LISTING

<160> NUMBER OF SEQ ID NOS: 1

<210> SEQ ID NO 1
<211> LENGTH: 53
<212> TYPE: DNA
<213> ORGANISM: Artificial sequence
<220> FEATURE:
<221> NAME/KEY: misc_feature
<223> OTHER INFORMATION: Polynucleotide

<400> SEQUENCE: 1
agggtaccta atacgactca ctatagggct agcaaagcgg ccgctctaga gac          53
```